United States Patent [19]

Eikmeier et al.

[11] Patent Number: 5,720,924

[45] Date of Patent: Feb. 24, 1998

[54] STORAGE SYSTEM FOR TEST ELEMENTS

[75] Inventors: Heino Eikmeier, Lorsch; Klaus-Dieter Sacherer, Kirchheim; Joerg Schreiber, Heddesheim; Wilfried Schmid; Hans-Juergen Kuhr, both of Mannheim, all of Germany

[73] Assignee: Boehringer Mannheim GmbH, Mannheim, Germany

[21] Appl. No.: 609,166

[22] Filed: Mar. 1, 1996

Related U.S. Application Data

[63] Continuation of Ser. No. 231,722, Apr. 22, 1994, abandoned.

[30] Foreign Application Priority Data

Apr. 23, 1993 [DE] Germany ............. 43 13 252.9
Aug. 27, 1993 [DE] Germany ............. 43 28 816.2

[51] Int. Cl.[6] ............................................. B01L 3/00
[52] U.S. Cl. .................. 422/102; 422/104; 221/25; 221/87; 206/569
[58] Field of Search ......................... 422/102, 104, 422/63, 58; 221/25, 30, 87; 271/264; 156/344, 584; 206/569; 435/805

[56] References Cited

U.S. PATENT DOCUMENTS

| | | | |
|---|---|---|---|
| 2,758,710 | 8/1956 | Arens | 206/56 |
| 3,759,374 | 9/1973 | Helger et al. | 206/65 R |
| 4,328,184 | 5/1982 | Kondo | 422/58 |
| 4,494,902 | 1/1985 | Kuppens et al. | 414/223 |
| 4,518,565 | 5/1985 | Boger et al. | 422/58 |
| 4,820,491 | 4/1989 | Khoja et al. | 422/63 |
| 4,965,983 | 10/1990 | Muller et al. | 53/435 |
| 5,090,591 | 2/1992 | Long | 221/25 |
| 5,102,008 | 4/1992 | Kaufman et al. | 221/25 |
| 5,176,880 | 1/1993 | Iwasaki et al. | 422/63 |
| 5,272,093 | 12/1993 | Silva et al. | 436/180 |
| 5,332,549 | 7/1994 | MacIndoe, Jr. | 422/63 |

FOREIGN PATENT DOCUMENTS

| | | |
|---|---|---|
| 57054838 | 9/1980 | Japan. |
| 721575 | 10/1952 | United Kingdom. |
| 93/02364 | 7/1991 | WIPO. |
| 93/07474 | 10/1991 | WIPO. |
| 94/01780 | 7/1992 | WIPO. |

OTHER PUBLICATIONS

Hinge action in polystyrene, Modern Packaging, Encyclopedia for 1964, p. 131.

*Primary Examiner*—Nina Bhat
*Attorney, Agent, or Firm*—Nikaido Marmelstein Murray & Oram LLP

[57] ABSTRACT

The system has several test elements, each of which is individually sealed to be impermeable to water vapor. The system storing test elements facilitates removal of test elements and protects the test elements contained in it against effects from the outside.

19 Claims, 3 Drawing Sheets

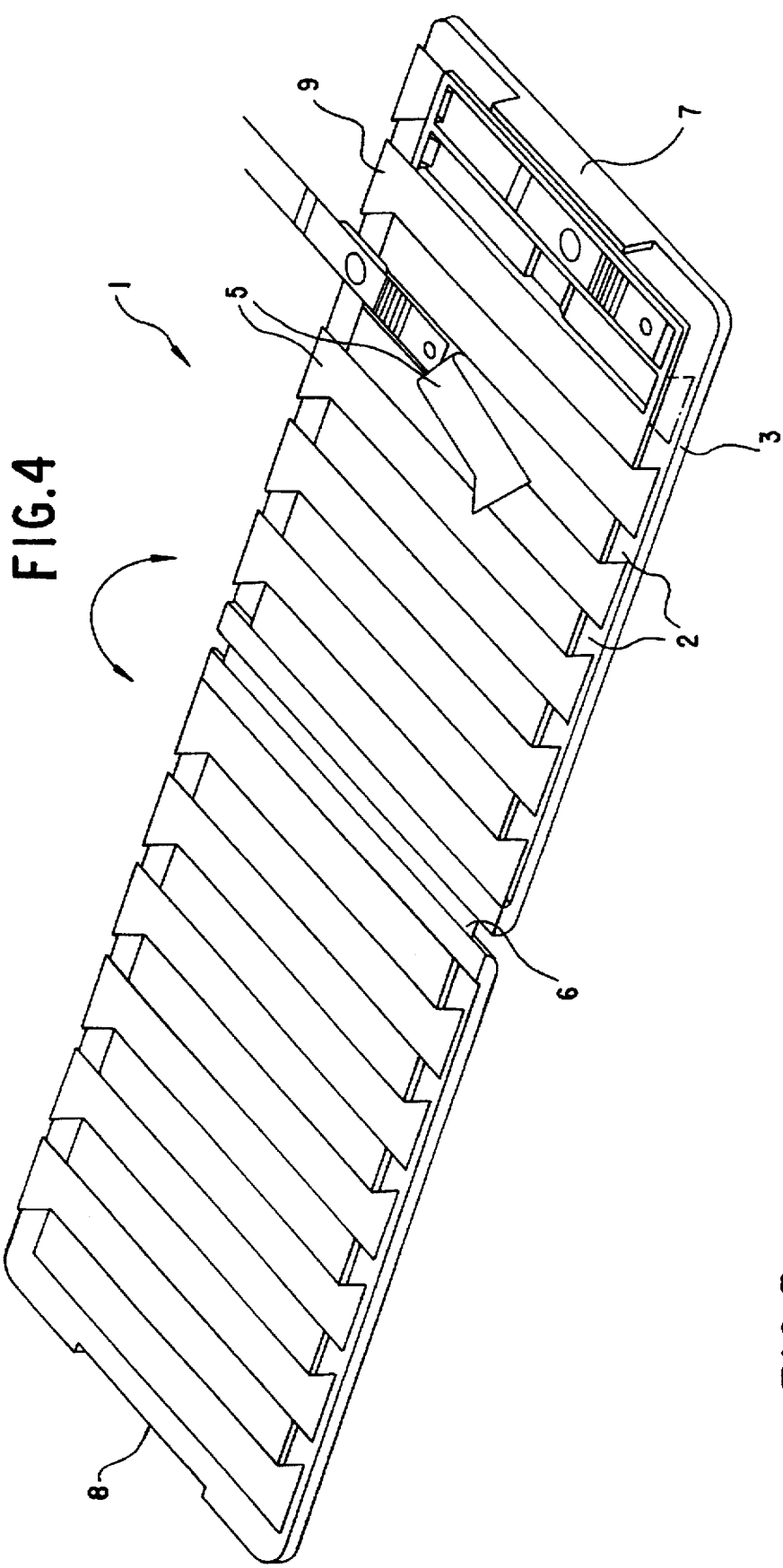
FIG. 4
FIG. 5

STORAGE SYSTEM FOR TEST ELEMENTS

This application is a continuation of application Ser. No. 08/231,722 filed Apr. 22, 1994 now abandoned.

FIELD OF THE INVENTION

The invention relates to a system for storing test elements or test strips where two or more individual test elements are kept in the chambers of it storage container, the chambers being impermeable to water vapor. The storage container is made of a rigid material and each chamber has one or several openings which are sealed by a foil so as to be impermeable to water vapor.

BACKGROUND OF THE INVENTION

Test elements are used, for example, in the field of clinical analysis to qualitatively and/or quantitatively detect components in body fluids. Particular importance is attached to test elements for the determination of blood glucose; such test elements are frequently provided in the form of test strips. Handy instruments for the determination of blood glucose in which the storage system of the invention could be used are commonly known.

Prior art test strips that are individually sealed in an aluminum laminate foil are known. To remove the test elements, the user tears open the foil and takes out the test element.

Further, it is known to store certain types of medication in the form of tablets. In so-called tablet blister packs, the tablets are individually sealed in chambers from which they can be removed by applying mechanical pressure. In this process, the tablet destroys the sealing.

The above-described prior art for storing and providing test elements has several drawbacks. Sealing test elements in aluminum laminates produces a lot of waste material and is relatively impractical for the user as tearing up the aluminum laminate often causes problems. Removing the test strips from the pack requires motor skills of the fingers which older and ill persons often lack. Automatic removal of test strips from flexible aluminum laminates by means of an automated device is only possible with great technical difficulties.

The sealing technology known from tablets cannot be applied to test elements as the test elements normally are flexible thin strips where pressing the test elements out of the sealing of a blister pack is not possible without problems.

SUMMARY OF THE INVENTION

The object of the invention is, to provide a system for storing test elements wherein the test elements can be individually sealed and from which they can be individually removed either manually or mechanically. Further, the system must ensure that the removal of test strips does not significantly reduce the storage stability of the remaining test strips. Moreover, the system should exclude deformation of test strips during removal from the system as far as possible.

The aforementioned objects are accomplished by a system for storing test elements for the analysis of sample liquids wherein two or more individual test elements are individually provided in the chambers of a storage container which are impermeable to water vapor, characterized in that the storage containers are made of a rigid material and each chamber has one or several openings which can be sealed by means of a foil so as to be impermeable to water vapor and the chambers are present in a regular geometric arrangement. Moreover, the invention also addresses a process for providing test elements.

The system of the invention comprises a storage container which has chambers that are separated from each other. The spatial separation of the chambers is an important feature of the invention as it greatly reduces the exchange of water vapor between the chambers. When a chamber is opened to remove a test strip, the test elements which remain in the system are thus not brought into contact with ambient air that may contain water vapor.

Form stability is another aspect of the storage container which is critical with respect to removing a test element. The chambers of the system are configured such that they surround a considerable part of the test strip while several chambers are rigidly connected to each other. In accordance with the invention, the chambers are present in a geometrically regular arrangement which, provided the system is used correctly, is not subject to deformation as it is the case with aluminum laminates, for example. An individual chamber preferably has the form of a tube whose cross section is essentially triangular or polygonal, or round or oval. Chambers with a rectangular cross section are particularly preferred. The preferred form of the cross section of the chambers is one that covers the test element along its longitudinal axis, but does not directly contact the test element at all sides thus allowing movement of the test elements in one or two directions. The chambers of a storage container in accordance with the invention are preferably continous with each other thus saving both space and material.

A geometrically regular arrangement in accordance with the invention is understood to be an arrangement in the form of a modular component, whereby a storage container system is created if several such elements are successively arranged.

The storage container system in accordance with the invention can be made of materials whose properties combine form stability and reduced permeability to water vapor. From the great number of materials which combine these two properties, those materials are preferred which can be easily used to obtain separate chambers. Preferred materials are plastics, such as polyethylene and polypropylene.

The chambers of the storage container have at least one, preferably two openings. If a test element has the form of a strip, the chamber openings are preferably located opposite a small edge of the test strip. The chamber openings can be parallel to the opposing sites of the test element. Advantageously, however, they form an acute angle together with the opposing side of the test element, preferably one between 1° and 45°.

The storage container in accordance with the invention preferably has 10 to 40 chambers to store a corresponding number of test elements.

In accordance with the invention, the openings of the chambers are sealed with a material that is impermeable to water vapor. In the invention, the terms impermeability to water vapor and reduced permeability to water vapor are understood to be properties that are relative. The properties identify the degree of usability of corresponding materials to provide a system where the test elements can be stored over several months without causing an unacceptable alteration of the test elements by means of water vapor.

Preferred materials for sealing the chambers are metal foils (e.g. aluminum foils), aluminum laminates, and plastics of a suitable thickness (usually >1 mm). These materials can be applied onto the openings of the chambers by means of gluing, melting, and pressing. In a preferred manner, some of the openings are adjacent to one another such that a piece of material of a corresponding size can be used to seal several openings.

The test elements for carrying out analysis are provided inside the chambers of the system. As test elements, particularly test strips, have been described comprehensively in prior art, they are not diseased in greater detail here. The system of the invention, however, can be advantageously used for test elements that are sensitive to bending or moisture.

Inside the chambers of the storage container, provision may be made for a drying agent to absorb moisture that may enter the system during manufacturing or penetrate the system despite the use of materials that are largely impermeable to water vapor. Suitable drying agents are solid drying agents which are known in prior art, particularly suitable are silica gels and molecular sieves.

In a first embodiment one or several devices to pierce the sealing of a chamber opening can be provided at the outside of the chambers. These devices can also be used to push the test element out of its chamber. In a preferred manner, the test element pierces the sealing at a second opening when pushed out. Devices for piercing the sealing can include, for example, plastic thorns that are affixed to the outside of the chambers. The sealing can be pierced by turning the respective thorn such that it rotates around an axis that is given by its connecting edge with the storage container.

In another embodiment, the thorn for piercing the sealing is affixed to the storage container such that it can be moved from chamber to chamber, each time piercing the respective chamber.

In an embodiment where a chamber preferably has only one opening, the sealing left of the chamber is peeled off and the test element contained in a chamber is taken out. Opening the sealing can be facilitated by providing a tab which can be broken and peeled off together with the foil. This principle is known, for example, from yogurt cups.

A data carrier for lot-specific data concerning the test elements and additional data concerning the analysis, e.g. expiration date and umber of strips in the system, can be provided at the outside of the system. This data can be present alphanumerically, in the form of a barcode or a magnetic strip.

Further, the invention comprises a process for providing test elements, wherein a sealed opening of a chamber is pierced and mechanical pressure is exerted on the test element contained in the chamber thus removing the test element from this chamber.

With the system of the invention it is possible to individually seal test elements. This means the sealing of one single test element can be broken, whereas the sealing of the test elements left in the system remains intact. The test elements can be removed in a most suitable manner, for example by manually or mechanically opening the opening of a chamber and removing the test element, for example by tilting the container. The sealing can be disrupted either by piercing the material or by peeling the sealing of the chamber off the opening.

A particularly preferred process is one where a first opening is pierced by a thorn or a lever, and a test element contained in the chamber is moved toward a second opening by means of a thorn or lever. If the thorn or lever exerts sufficient pressure onto the test element, the latter pierces the second sealed opening to exit the storage container. The piercing of the second sealing by the test element can be accomplished in a particularly simple manner if the sealing and its opposing edge of the test element form an acute angle. In this arrangement, the sealing is first pierced by a corner of the test element and then completely opened by the edge of the element.

As compared to already existing forms of packaging, the system of the invention has the advantage that all test elements can be removed individually either manually or by means of a device, while the test elements which remain in the system are further protected from moisture. Also, as compared to already existing forms of packaging, it is considerably easier to remove test strips from the system of the invention.

BRIEF DESCRIPTION OF THE DRAWINGS

FIG. 4 is a system when opened in accordance with embodiment III.

FIG. 5 is a system when closed in accordance with embodiment III.

DESCRIPTION OF THE PREFERRED EMBODIMENTS

Embodiment I

Figure 1:
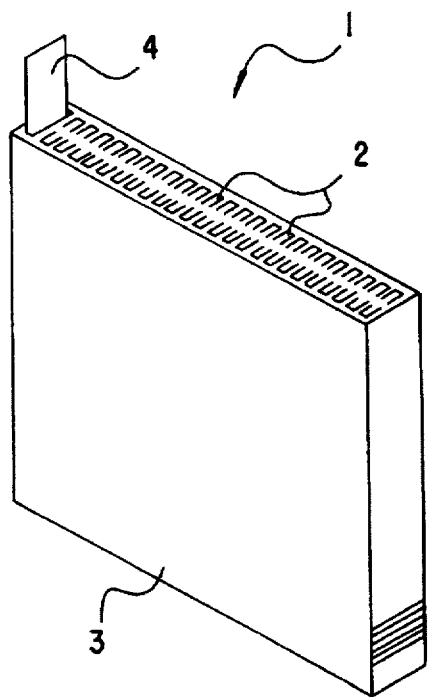
FIG. 1 is a perspective representation of a system in accordance with embodiment I.

FIG. 1 is a perspective view of a system (1) in accordance with the invention. The chambers (2) of the storage container (3) have the form of tubes with a rectangular cross section. The test elements (4) contained in the chambers (2) are arranged parallel one after another. The storage container is made of polyethylene and was manufactured in an injection molding procedure. A foil made of aluminum laminate for sealing the openings of the chambers at the top and bottom of the storage container (3) was applied by means of ultrasonic welding.

Figure 2:
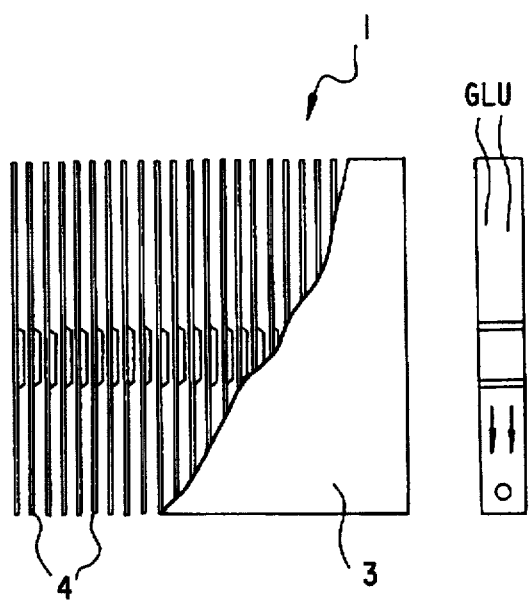
FIG. 2 is a lateral view of the storage contain with test elements in accordance with embodiment I.

FIG. 2 is a lateral view of the system (1) of the invention in a partial section. This representation emphasizes in particular the space-saving packaging of the test elements (4) due to their successive arrangement.

Embodiment II

Figure 3:
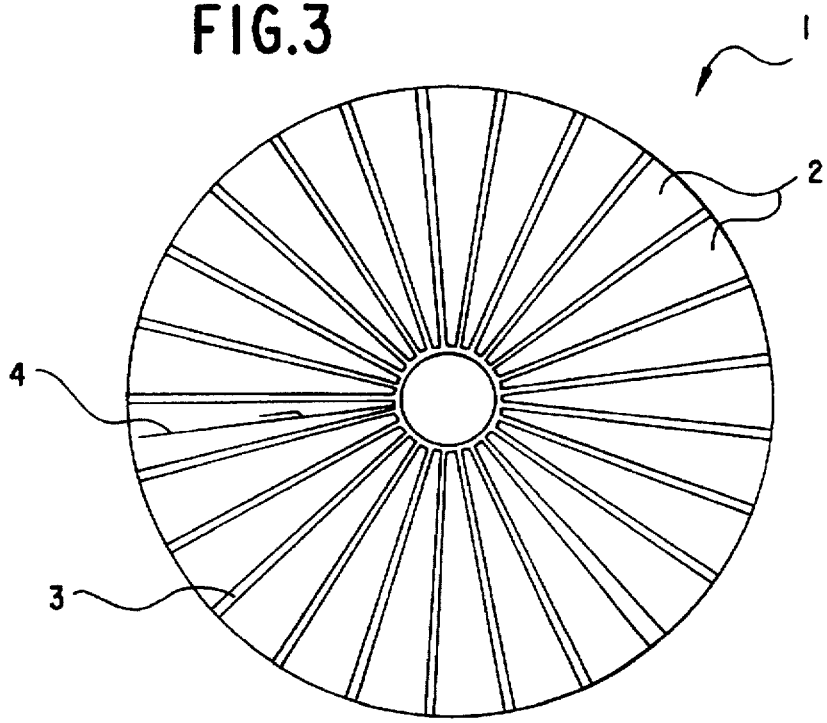
FIG. 3 is a cross section of a system in accordance with embodiment II.

FIG. 3 shows a system (1) where the cross sections of the chambers (2) have the form of circular segments. The longitudinal test elements (4) can either be arranged as shown in the drawing where the longitudinal axis of the test elements (4) is directed away from the center of the circle toward the outside or such that the circular axis of the storage container (3) and the longitudinal axis of the test elements (4) are provided in a parallel arrangement. In the former case, the system has the form of a relatively flat circular disk, whereas in the second case it has the form of a longitudinal cylinder.

Embodiment III

FIG. 4 shows a system (1) of the invention in the form of a snap-shut case. Chambers (2) are formed like longitudinal boxes with one side wall being open. Each chamber has, hence, one opening that is sealed with a sealing foil (5) made of aluminum laminate. At one side of the opening, below the foil, provision is made for a lever (9) which is connected to the plastic casing of the storage container (3) by means of a connection with a designated breaking point. To remove a test element (4), the lever (9) is folded down and peeled off together with the sealing foil (5).

The storage container (3) comprises two parts, connected via a hinge (6). To store the system (1), both parts of the storage container (3) can be snap-shut with a closing profile (7) engaging a recess in the material (8) thus keeping the system shut.

Figure 6C:
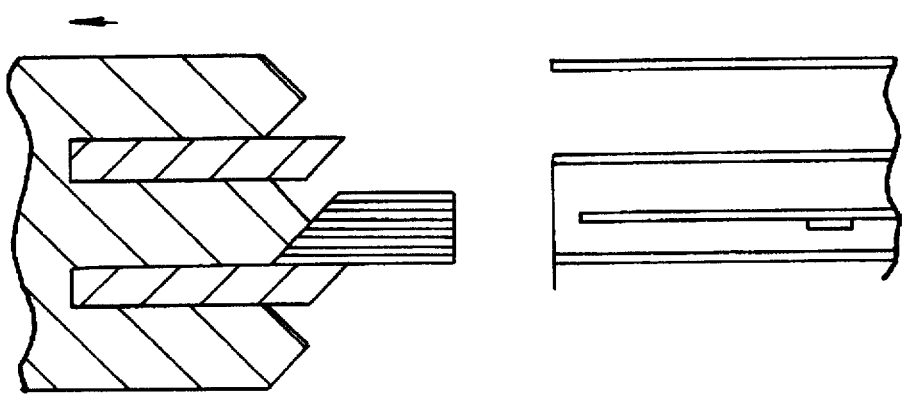
FIGS. 6(A)–6(C) demonstrate the function of the device for removing test elements from the system in accordance with embodiment I.
Figure 6B:
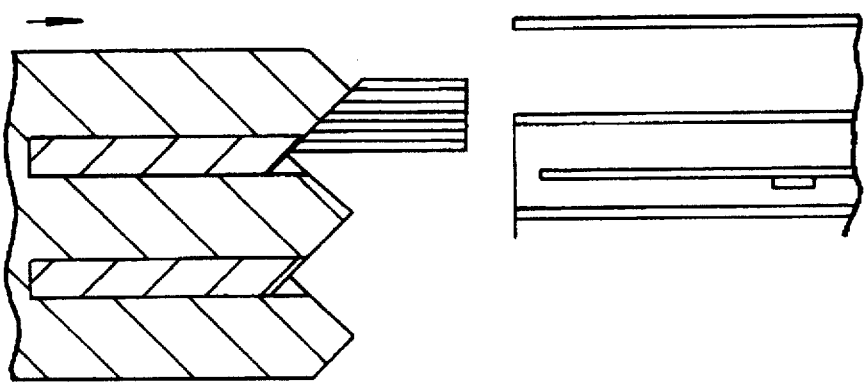
Figure 6A:
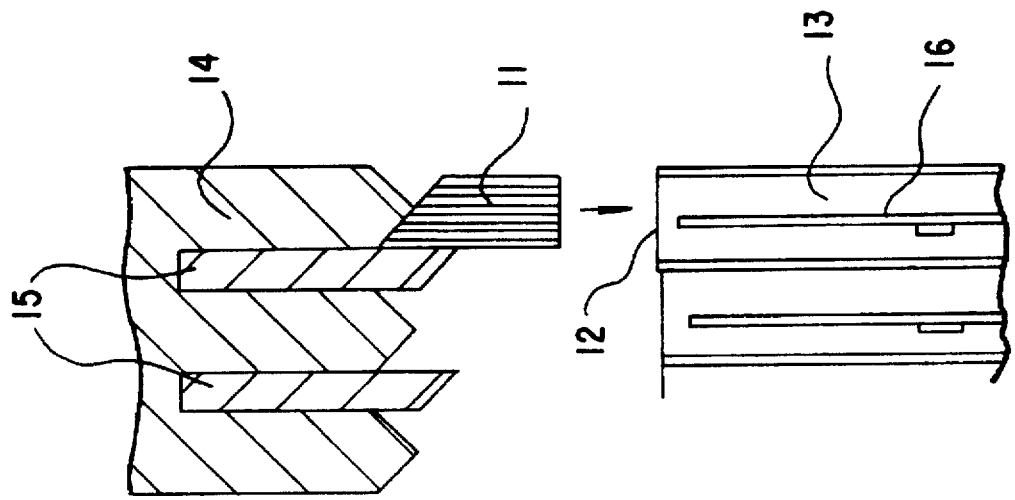

FIG. 5 shows the system of FIG. 4, when closed. The openings of the chambers of the system are located at the inner side of the storage container, such that the sealing foils of unused test elements are protected from external damage. Device for removing test elements:

FIGS. 6(A)–6(C) are diagrammatic representations illustrating how a device for removing test elements from the system (1) functions. A small ram (11) is disposed opposite the sealed opening (12) of a chamber (13). The device is activated by exerting pressure onto cover (14) of the removal device in direction toward opening (12) (FIG. 6A). The small ram (11) pierces the sealing of opening (12) and pushes the test element (16) out of chamber (13). While the cover (14) is moved, the guiding pins (15) remain in position which causes the cover (14) and guiding pins (15) to form a ramp after assuming the end position of the movement. The ram (11) is then moved sideways on this ramp (FIG. 6B).

If the cover (14) is moved back into its initial position, it forms a second ramp on which the ram (11) is again moved sideways in the same direction to snap into a new resting position (FIG. 6C). The distances between the projecting parts of cover (14) and guiding pins (15) are dimensioned such that the ram, after going through movements A, B, and C, is located opposite a new chamber opening.

List of Reference Numerals (1) system
(2) chamber
(3) storage container
(4) test element
(5) sealing foil
(6) hinge
(7) closing profile
(8) recess in material
(9) lever
(11) small ram
(12) sealed opening
(13) chamber
(14) cover
(15) guiding pins
(16) test element

We claim:

1. A storage system for test elements for analyzing sample liquids, comprising:
   a rigid storage container including a plurality of tubes having two ends, the tubes having longitudinal axis which are parallel to one another, and the tubes having openings at the two ends thereof;
   foils sealing said openings of said tubes, said foils sealing interiors of said tubes from water vapor from the surroundings wherein said tubes and foils form water vapor-impermeable chambers; and
   a plurality of test elements individually located in a respective water vapor-impermeable chamber, wherein an angle of 1° to 45° is formed between an end of each test element and the opening opposite the end of the test element.

2. A storage system of claim 1, wherein the chamber openings are rendered impermeable to water vapor by being sealed by a foil of aluminum or laminate thereof which is applied to the rigid storage container by gluing, pressing or welding.

3. The storage system of claim 1, wherein the rigid storage container is cylindrical, and cross sections of the chambers are in the form of circular segments.

4. The storage system of claim 1, further including a piercing device for piercing the sealing foil of the sealed chambers.

5. The storage system of claim 4, wherein the piercing device comprises a ram, guiding pins for guiding said ram and a cover, wherein pressure can be applied to the cover which transmits a force to the ram to cause the ram to pierce the sealing foil.

6. The storage system of claim 1, wherein a drying agent is contained in each chamber.

7. The storage system of claim 1, wherein the angle between the end of the test strip and the opening opposite the end of the test strip is 5° to 45°.

8. The storage system of claim 1, wherein a data carrier is fixed to the rigid storage container.

9. A storage system according to claim 1, wherein each said chamber covers test element inside along the longitudinal axis, but does not directly contact said test element at all sides.

10. A storage system according to claim 1, wherein said test strip is removable from the tube through either of said two openings.

11. A process for providing a test element which has not been exposed to deleterious amounts of water vapor, said method comprising
    providing a plurality of test elements in sealed chambers of the system of claim 1,
    pealing a sealing foil off of at least part of an opening of a first chamber to expose a test element contained in the first chamber; and
    removing the test element from the first chamber.

12. A process for providing a test element which has not been exposed to deleterious amounts of water vapor, said method comprising
    providing a plurality of test elements in sealed chambers of the system of claim 1,
    piercing a foil sealing an opening of a first chamber of said system; and
    exerting mechanical pressure on the test element in the first chamber to, cause the test element to pierce a second foil of a second opening of the first chamber to push the test element out of the first chamber.

13. Process of claim 12, wherein the test element is pushed from the first chamber directly into an instrument for analyzing the sample liquids.

14. A storage system for test elements for analyzing sample liquids, comprising;
    a rigid storage container including a plurality of tubes having two ends, the tubes having longitudinal axis which am parallel to one another, and the tubes having openings at the two ends thereof;

foils sealing said openings of said tubes, said foils sealing interiors of said tubes from water vapor from the surroundings wherein said tubes and foils form water vapor-impermeable chambers;

a plurality of test elements individually located in a respective water vapor-impermeable chamber; and pushing means for pushing a first end of one of the test elements such that a second end of the test element pierces a foil sealing the opening of the tube which is opposite the second end of the test element.

15. The storage system according to claim 14, wherein an angle is formed between an end of each test element and the opening opposite the end of the test element.

16. The storage system according to claim 15, wherein the angle is between 1° to 45°.

17. A storage system according to claim 14, wherein said pushing means pierces a foil sealing the opening of the tube which is opposite the first end of the test element.

18. A storage system according to claim 14, wherein said storage container is cylindrical.

19. A storage system according to claim 14, wherein said piercing means comprises a ram, guiding pins for guiding said ram and a cover, wherein pressure can be applied to the cover which transmits a force to the ram to cause the ram to pierce a foil.

* * * * *